Jan. 31, 1956 G. J. VON ABRAMS Plant Pat. 1,455
ROSE PLANT
Filed March 14, 1955
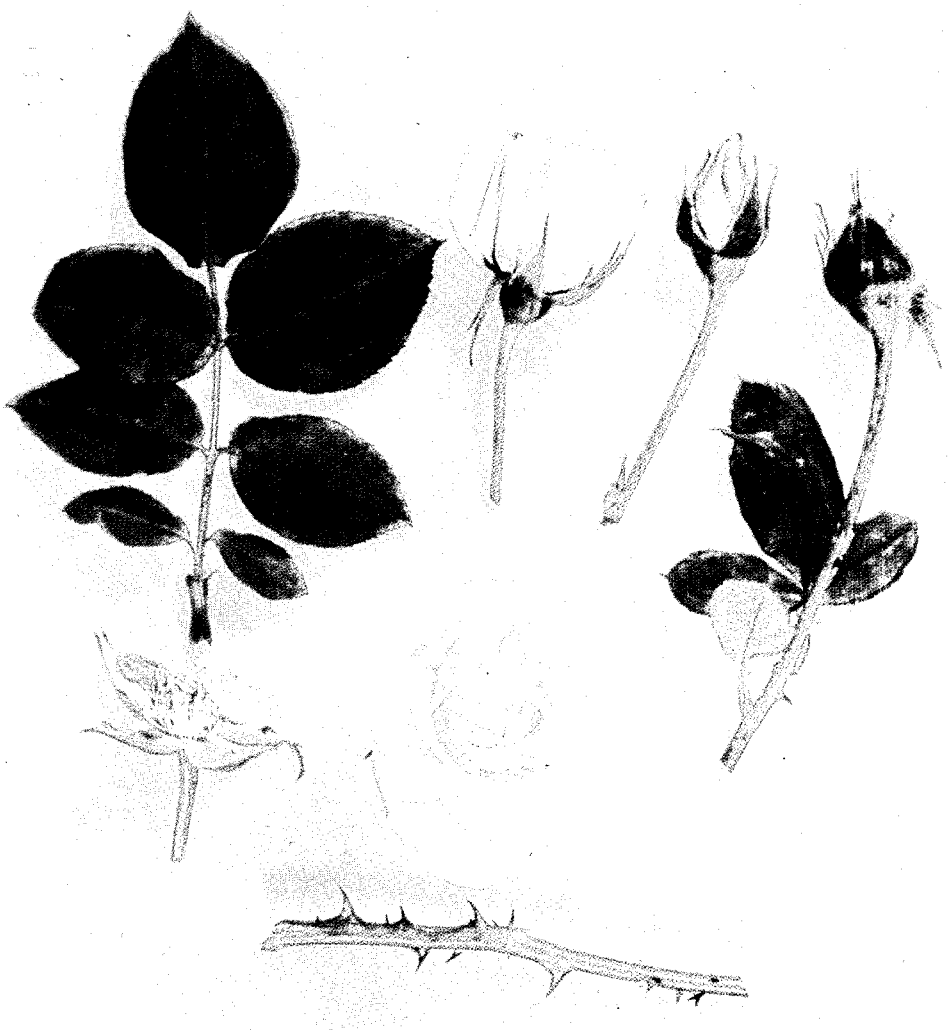
Inventor
G. J. Von Abrams
By: Robb & Robb
Attorneys.

United States Patent Office

Plant Pat. 1,455
Patented Jan. 31, 1956

1,455

ROSE PLANT

Gordon J. Von Abrams, Scappoose, Oreg., assignor to Eldon Pinkeney Dering, doing business as Peterson & Dering, Scappoose, Oreg.

Application March 14, 1955, Serial No. 494,301
1 Claim. (Cl. 47—61)

The present invention relates to a new and distinct variety of rose plant of the floribunda (hybrid tea—hybrid Moschata) class which was originated by me by crossing the variety "Show Girl" (Plant Patent No. 646) with the variety "Fashion" (Plant Patent No. 789).

The primary objective in making this cross was to produce a new variety of rose plant having the general habits of the parent variety "Fashion," but which bears flowers which are more nearly pink in color and more high-centered in form than the flowers of that variety. This objective was fully achieved, along with other improved and desirable characteristics, which, taken together, represent a unique and desirable combination of outstanding features.

Briefly stated, the new variety is phenotypically characterized by the following:

(1) The compact, low-growing but vigorous and well-branched bush form of the plant which averages from 2 to 3 feet in height;

(2) Its habit of bearing the flowers in loosely-formed clusters of from small to medium size;

(3) The unique combination of form and distinctive pink color of the flowers, which is different from that of any other rose variety known to me;

(4) Its moderate to heavy flower productivity throughout the growing season; and (5) The abundant foliage and good distribution thereof on the plant.

In comparison with its seed parent, "Show Girl," the plant of my new variety is more compact and much smaller; the mature foliage is smaller, but otherwise quite similar; the flowers have many more petals, but the petals are smaller and shorter in length; both the flowers and the buds are smaller throughout their entire development; the form of both the bud and the newly open flower is less elongate; and the color of the flower is somewhat lighter and less blue than the color of the flower of this parent variety.

As compared with its pollen parent, "Fashion," the young foliage of the new variety is smaller and brighter in color, with more yellow and less red color, while the mature foliage is larger, broader, more rounded in outline, less sharply serrate and very slightly lighter in color; the open flowers are larger, more high-centered, have more petals and are more blue in color, with less yellow pigment; the peduncle is long and stout and slightly less glandular; and the thorns are generally similar in size and color, but are more numerous than the thorns of this parent variety.

Asexual reproduction of my new variety by budding, as performed by me at Scappoose, Oregon, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated as "Wilson") and Robert Ridgway's Color Standards and Nomenclature (hereinafter abbreviated as "Ridgway"), as indicated, except where general color terms of ordinary dictionary significance are obvious:

Type: Hardy; compact; bush; outdoor; seedling; for cut flowers and for garden decoration.

Class: Floribunda (hybrid tea—hybrid Moschata).

Breeding:

*Seed parent.*—"Show Girl."

*Pollen parent.*—"Fashion."

Propagation: Holds its distinguishing characteristics through succeeding propagations by budding.

FLOWER

Locality where grown and observed: Scappoose, Oregon.

Flowers borne: Several to stem; in rounded clusters; on strong, long stems.

Quantity of bloom: Abundant, outdoors.

Continuity: Continuous.

Fragrance: From slight to penetrating.

Bud:

*Peduncle.*—Short; from 3 to 4½ cm.; medium diameter; erect; moderately rough; with several glandular cilia; no prickles. Color—near Calliste Green, Plate VI, 31. i. (Ridgway), but sometimes reddish.

*Before calyx breaks.*—Size—from small to medium (about 1.3 x 2 cm., including receptacle). Form—short; pointed; with moderately conspicuous neck; no foliaceous appendages on surface of bud, but with 1, and frequently 2, long (4 mm.), slender foliaceous appendages on the lateral margins of alternate sepals; usually with very slight foliaceous parts extending beyond the tip of the bud less than ¼ of its length. Color (receptacle)—near Calliste Green, Plate VI, 31. i. (Ridgway), with sepals flushed with Maroon, Plate I, 3. m. (Ridgway).

*As calyx breaks.*—Color—near Pomegranate Purple, Plate XII, 71. i. (Ridgway).

*As first petal opens.*—Size—medium. Form—ovoid. Color: outside—Rose Doree, Plate I, 3. b. (Ridgway), with basal spot of Empire Yellow, Plate IV, 21. b. (Ridgway); inside—from Rose Madder, Plate 23/1, page 23 (Wilson) to Rose Madder, Plate 23/2, page 23 (Wilson); infrequently with irregular darker markings of near Rose Red, Plate 724, page 158 (Wilson).

*Opening.*—Opens up well under all normal weather conditions.

Bloom:

*Size (when fully open).*—From 2½ to 3¼ inches.

*Petalage.*—Double; from 35 to 42 petals; arranged quite regularly.

*Form.*—High-centered, and remaining high-centered to senescence; petals begin to roll outward at apex as they open, and the rolling quickly extends to the lateral margins, beginning as a tight, short roll, relaxing very little, and remaining short at maturity.

Petals: Moderately thick; with inside slightly velvety and outside satiny.

*Shape.*—Outside—broadly ovate; nearly round; with margin entire to irregularly scalloped. Intermediate—broadly ovate, with apex mucronate. Inside—slender ovate, with apex mucronate.

This description of a newly opened flower was made from a rose grown outdoors in the month of July, at Scappoose, Oregon:

*Color.*—Outside petal: Outer surface—near Tyrian Rose, Plate 24/1, page 24 (Wilson) near base, shading to Neyron Rose, Plate 623/1, page 76 (Wilson) at apex; basal flush of Buttercup Yellow, Plate 5/2, page 5 (Wilson), and nearly white at margins. Inner surface—between Eosine Pink, Plate I, 1. d. (Ridgway) and La France Pink, Plate I, 3. f. (Ridgway); basal flush near Empire Yellow, Plate IV, 21. b. (Ridgway), and nearly white at margins. Intermediate petal—apical and lateral edges of petals have narrow white or nearly white margins on both surfaces. Outer surface—near Carmine, Plate 21/1, page 21 (Wilson) near base, shading to Hermosa Pink, Plate I, 1. f. (Ridgway) above; small basal flush of pale yellow, with nearly white margins. Inner surface—between Eosine Pink, Plate I, 1. d. (Ridgway) and La France Pink, Plate I, 3. f. (Ridgway); basal flush near Empire Yellow, Plate IV, 21. b. (Ridgway), with nearly white margins. Inside petal—apical and lateral edges of petals have narrow white or nearly white margins on both surfaces. Outer surface—near Neyron Rose, Plate 623/2, page 76 (Wilson), with some Phlox Pink, Plate 625, page 77 (Wilson) flush near base; basal flush of pale yellow with white margins. Inner surface—between Eosine Pink, Plate I, 1. d. (Ridgway) and La France Pink, Plate I, 3. f. (Ridgway), with Strawberry Pink, Plate I, 5. d. (Ridgway) flush near base, at first, changing quickly to nearly white; pale yellow basal flush, near white at edges.

This description was made from a rose that was open for 3 days outdoors in the month of July, at Scappoose, Oregon:

*Color.*—Outside petal: Outer surface—Phlox Pink, Plate 625/1, page 77 (Wilson), with a lighter flush of Phlox Pink, Plate 625/3, page 77 (Wilson) or lighter along veins; sometimes irregularly marked with deeper color near Phlox Pink, Plate 625, page 77 (Wilson); basal flush nearly white. Inner surface—Hermosa Pink, Plate I, 1. f. (Ridgway), with nearly white flush at base; frequently darker, near Carmine Rose, Plate 621, page 75 (Wilson) toward apex. Intermediate petal: Outer surface—from Neyron Rose, Plate 623/1, page 76 (Wilson) to Phlox Pink, Plate 625/2, page 77 (Wilson); lighter color along veins and nearly white at base. Inner surface—from Neyron Rose, Plate 623/2, page 76 (Wilson) where covered by adjacent petals to Carmine Rose, Plate 621, page 75 (Wilson) where exposed; nearly white at base. Inside petal: Outer surface—from Neyron Rose, Plate 623/1, page 76 (Wilson) to Phlox Pink, Plate 625/2, page 77 (Wilson); lighter color along veins and nearly white at base. Inner surface—La France Pink, Plate I, 3. f. (Ridgway).

*General color effect.*—Carmine Rose, Plate 621/1, page 75 (Wilson).

*Behavior.*—Drop off cleanly.

*Flower longevity.*—On bush in garden—8 days in July. Cut roses grown outdoors and kept at room temperature—6 days in July.

REPRODUCTIVE ORGANS

Stamens: Many; arranged regularly about pistils on margin of receptacle.

Filaments: Medium length (about 9 mm.); nearly all with functional anthers.

*Color.*—Near Apricot Yellow, Plate IV, 19. b. (Ridgway).

Anthers: Medium size (about 1 x 2 mm.); all open nearly at same time.

*Color.*—Near Light Orange Yellow, Plate III, 17. d. (Ridgway).

Pollen: From moderate to abundant.

*Color.*—Variable gold.

Pistils: Moderate number (about 75).

Styles: Even; medium length (about 8 mm.); medium heavy; loosely bunched.

Stigma:

*Color.*—Pale yellow.

Ovaries: All enclosed in receptacle.

Fruit: From short to globular, with inconspicuous neck; moderately smooth; walls medium thin and fleshy.

*Color (at maturity).*—Orange.

Seeds: Moderate number; medium size.

Sepals: Persistent; not permanent; moderately long (about 18 x 8 mm.); spear-shaped; from straight to slightly curled laterally, and slightly recurved toward stem; with glandular marginal appendages on non-adjacent margins (about 5 x 1 mm.); with numerous glandular cilia on external surface; with short (about 5 mm.) apical appendages.

*Color (at flower maturity).*—Outside—between Calliste Green, Plate VI, 31. i. (Ridgway) and Scheele's Green, Plate VI, 33. i. (Ridgway), heavily flushed with maroon which sometimes masks the green color. Inside—near Light Grape Green, Plate XLI, 25'''. b. (Ridgway); sometimes flushed with maroon.

PLANT

Foliage:

*Leaves.*—Usually composed of 5 leaflets; abundant; moderately heavy; leathery.

*Leaflets.*—Medium size (about 4.5 x 7 cm.); ovate; apex slightly mucronate; base obtuse, but sometimes slightly cordate; margin irregularly serrate.

*Color.*—Mature: Upper surface—darker than Spinach Green, Plate 0960, page 187 (Wilson). Under surface—near Asphodel Green, Plate XLI, 29''' (Ridgway). Young: Upper surface — between Calliste Green, Plate VI, 31. i. (Ridgway) and Parrot Green, Plate VI, 31. k. (Ridgway), with lateral red flush. Under surface — near Indian Lake, Plate XXVI, 71'. i. (Ridgway), with near Rinnemann's Green, Plate XVIII, 31'. i. (Ridgway) along midrib and veins.

*Rachis (the supporting stem of the compound leaf).*—Medium heavy. Upper side—grooved, with several glandular cilia on margins. Under side—few glandular cilia; few thorns.

*Stipules.*—Size about 15 x 5 mm. or smaller; with short points turning out at an angle of less than 45°.

*Disease resistance.*—Above average resistance to mildew, as determined by field observations and comparisons with other varieties grown under comparable cultural conditions at Scappoose, Oregon.

Growth:

*Habit.*—Compact; bush; much-branched.

*Growth.*—Free.

*Canes.*—Medium heavy.

*Main stems.*—Color—dull corky brown. Thorns—several; medium size; slightly hooked downward; with normal base. Prickles—none. Hairs—none.

*Branches.* — Color — dull green. Thorns—several; medium size; slightly hooked downward; with normal base. Prickles—none. Hairs—none.

*New shoots.*—Color—bright green, flushed with maroon. Thorns—several; medium size; slightly hooked downward; with short base. Prickles—none. Hairs—none.

I claim:

A new and distinct variety of rose plant of the floribunda class, substantially as herein shown and described, characterized particularly as to novelty by its compact, low-growing but vigorous and well-branched habits of growth, the abundance and good distribution of its foliage, its moderate to heavy flower productivity throughout the growing season, the loosely formed cluster habit of its flowers, with the clusters varying from small to medium size, and the unusual and distinctive combination of form and color of its high-centered pink flowers.

No references cited.